US012715836B2

(12) United States Patent
Galvão Siqueira et al.

(10) Patent No.: US 12,715,836 B2
(45) Date of Patent: Aug. 25, 2026

(54) NITRATES OF ETHERS OF GLYCEROL AND ETHANOL AS DIESEL CETANE IMPROVERS AND THE PRODUCTION PROCESS OF THE SAME

(71) Applicant: Petróleo Brasileiro S.A.—Petrobras, Rio de Janeiro (BR)

(72) Inventors: Bernardo Galvão Siqueira, Rio de Janeiro (BR); Cristiana Neves Porto, São João de Meriti (BR); Raphael Bezerra De Menezes, Rio de Janeiro (BR); Marlito Gomes Junior, Petropolis (BR); Carlos Rene Klotz Rabelo, Rio de Janeiro (BR)

(73) Assignee: Petróleo Brasileiro S.A.—Petrobras, Rio de Janeiro (BR)

( * ) Notice: Subject to any disclaimer, the term of this patent is extended or adjusted under 35 U.S.C. 154(b) by 1103 days.

(21) Appl. No.: 17/781,328

(22) PCT Filed: Nov. 19, 2020

(86) PCT No.: PCT/BR2020/050488
§ 371 (c)(1),
(2) Date: May 31, 2022

(87) PCT Pub. No.: WO2021/102542
PCT Pub. Date: Jun. 3, 2021

(65) Prior Publication Data

US 2023/0002309 A1 Jan. 5, 2023

(30) Foreign Application Priority Data

Nov. 28, 2019 (BR) .......................... 1020190251735

(51) Int. Cl.
*C07C 203/04* (2006.01)
*C07C 201/02* (2006.01)
*C10L 1/23* (2006.01)

(52) U.S. Cl.
CPC .......... *C07C 203/04* (2013.01); *C07C 201/02* (2013.01); *C10L 1/231* (2013.01); *C10L 2200/0446* (2013.01); *C10L 2230/22* (2013.01)

(58) Field of Classification Search
CPC ...... C07C 203/04; C07C 201/02; C10L 1/231
See application file for complete search history.

(56) References Cited

U.S. PATENT DOCUMENTS

| | | | |
|---|---|---|---|
| 2,066,506 | A | 1/1937 | Woodbury et al. |
| 2,294,849 | A | 9/1942 | Olin et al. |
| 3,968,139 | A | 7/1976 | Reed, Jr. |
| 4,448,587 | A | 5/1984 | Hinkamp et al. |
| 4,536,190 | A | 8/1985 | Seemuth et al. |

FOREIGN PATENT DOCUMENTS

| | | | |
|---|---|---|---|
| BR | PI0803767-1 | A2 | 3/2010 |
| BR | PI0803522-9 | A2 | 6/2010 |
| BR | 102015010092 | A2 | 11/2017 |
| EP | 0116197 | A2 | 8/1984 |
| GB | 993623 | A | 6/1965 |

OTHER PUBLICATIONS

Eremenko et al. Synthesis and Study of Some Physical Properties of 1-n-alkyl Ethers of Glycerol and Their Dinitrates., Chem. Bull. 26, 399-401. (Year: 1977).*
International Search Report, issued by International Searching Authority in corresponding International Application No. PCT/BR2020/050488, mailed Feb. 18, 2021.
Written Opinion of the International Searching Authority, issued by International Searching Authority in corresponding International Application No. PCT/BR2020/050488, mailed Feb. 18, 2021.

* cited by examiner

*Primary Examiner* — Sikarl A Witherspoon
(74) *Attorney, Agent, or Firm* — ArentFox Schiff LLP

(57) ABSTRACT

The present invention is related to the use of nitrates of ethers of glycerol and ethanol as diesel cetane improvers, and the production process of the same, aiming at producing an additive from glycerol from biodiesel production and bringing to the additive market an option more economical and efficient to facilitate the ignition of diesel and improve the cetane number of said fuel.

10 Claims, 2 Drawing Sheets

NITRATES OF ETHERS OF GLYCEROL AND ETHANOL AS DIESEL CETANE IMPROVERS AND THE PRODUCTION PROCESS OF THE SAME

CROSS-REFERENCE TO RELATED APPLICATIONS

This application is a National Stage entry of International Application No. PCT/BR2020/050488, filed on Nov. 19, 2020 which claims priority to Brazilian Patent Application No. BR 1020190251735, filed on Nov. 28, 2019. The disclosures of the priority applications are hereby incorporated in their entirety by reference.

FIELD OF THE INVENTION

The present invention is related to nitrates of ethers of glycerol and ethanol as diesel cetane improvers, and the production process of the same. The invention proposed here aims at providing an additive produced from glycerol from the production of biodiesel and to bring to the additive market a more economical and efficient option to facilitate the ignition of diesel and improve the cetane number in said fuel.

DESCRIPTION OF THE STATE OF THE ART

Currently, environmental and legislative restrictions drive the development of biodiesel in the world. However, its production generates a series of by-products of low added value, among which it is possible to mention glycerin, which represents about 10% by weight of biodiesel production. Thus, for each ton of biodiesel produced, about 100 kg of glycerin are generated, which may vary according to the raw material used.

Considering that, in Brazil, Law No. 13,263/2016 determines a schedule for a progressive increase in the biodiesel content in diesel, from 8% in 2017 to 9% in 2018 and, finally, 10% in 2019, a great opportunity for the development of new applications to the surplus of glycerin generated is created.

From another point of view, more modern engines demand better quality fuels, which is reflected in the need for increasingly higher cetane numbers, since the progressive increase in this specification is directly linked to greater fuel economy, better cold start, lower emission of particulates and noise from the engine.

Among the various compounds used as cetane-improving additives, 2-ethyl hexyl nitrate (2-EHN) stands out. This compound, used all over the world, is produced from the nitration of 2-ethyl-hexanol (2-EH), a superior alcohol basically obtained from the hydroformylation of propene with synthesis gas ($CO/H_2$). This raw material has a high cost and is also used in the production of plasticizers for polymers and esters.

In general, the companies producing 2-EHN dominate the entire production chain from the raw material to its distribution in the refineries. In Brazil, all the 2-EHN used to adapt the diesel to the specification of the Brazilian National Agency of Petroleum, Gas and Biofuels (ANP) is imported.

With respect to the universe of nitrates and their use as additives, it is important to highlight the document U.S. Pat. No. 2,294,849 that addresses to methods of preparing nitrates from various alcohols, aiming at using them as cetane improvers.

In the same context, patent GB 993623 points out the positive effect of nitrates of aliphatic alcohols of up to 5 carbon atoms in the increase of cetane in diesel compared to other nitrates of superior carbon chain. Likewise, U.S. Pat. No. 4,448,587 describes the synergistic effect of mixing aliphatic alcohol mono-nitrates with alcohol alkylated nitrates on increasing the cetane number in diesel.

Still in relation to additives, document PI 0803767-1 addresses to the production of glycerin ethers from the glycerin etherification reaction, under heterogeneous catalysis conditions, aiming at obtaining, with high selectivity, glycerol mono-ether, in particular glycerin tert-butyl ether. Said glycerol mono-ether is added to the fuel as an additive and the proposal is to obtain the additive from glycerin and tert-butanol. However, the document under analysis does not propose the nitration of the final additive.

Another document to be mentioned is PI 0505472-9, which addresses to a process and additive to increase the cetane number of the diesel. The additive is obtained from the reaction of an alkene or alkyne with glycerin, coming or not from the production of biodiesel. However, the process referring to document PI 0505472-9 does not dispense with the use of hydrocarbons for the production of the claimed additive.

From the mentioned documents, it appears that nitrated additives have superior performance with regard to the cetane number. Furthermore, the specialized literature SIRIPRAPAKIT et al., 2009, compares nitrated compounds with dinitrated compounds, showing the superiority of dinitrated compounds over nitrated ones, including against 2-ethyl hexyl nitrate, currently used in the market.

From the disclosure above, there is a need to obtain dinitrated compounds from glycerol, in order to optimize the properties of diesel and give a specific destination for the glycerol from the production of biodiesel.

BRIEF DESCRIPTION OF THE INVENTION

The production process of nitrates from glycerol ethers and ethanol to be used as diesel cetane improvers uses reagents with a high supply on the market, namely glycerol and ethanol, according to the steps described below:

(a) etherification reaction of ethanol with glycerol, whether or not from the biodiesel production process, using acidic catalysts, which can be chosen from: ion exchange resins, zeolites, aluminas, niobic acid or others, in a batch reactor (STR), continuously fed (CSTR), fixed bed or reactive distillation;

(b) separation of the reactor effluent from step (a), by traditional unit operations, in order to obtain the glycerol and ethanol mono-ethers in a concentrated form. The glycerol di- and tri-ethers produced can be sent to the diesel pool or to other applications such as solvents and bases for paints and cleaning products. The di-ethyl ether formed could also be used as a fuel or sold for more specific applications;

(c) nitration of the glycerol and ethanol mono-ethers separated in step (b), which, in this way, are subjected to nitration of their two available hydroxyl groups, forming dinitrated ethers, specifically 1-ethoxy-2,3-propanediol dinitrate or 2-ethoxy-1,3-propanediol dinitrate.

The addition of said glycerin and ethanol dinitrates to diesel allows to reach the specified cetane number using smaller amounts of additive when compared to the use of conventional additives.

BRIEF DESCRIPTION OF DRAWINGS

The present invention will be described in more detail below, with reference to the attached figures that, in a schematic way and not limiting the inventive scope, represent examples of its embodiment. In the drawings, there are.

DETAILED DESCRIPTION OF THE INVENTION

Figure 1:
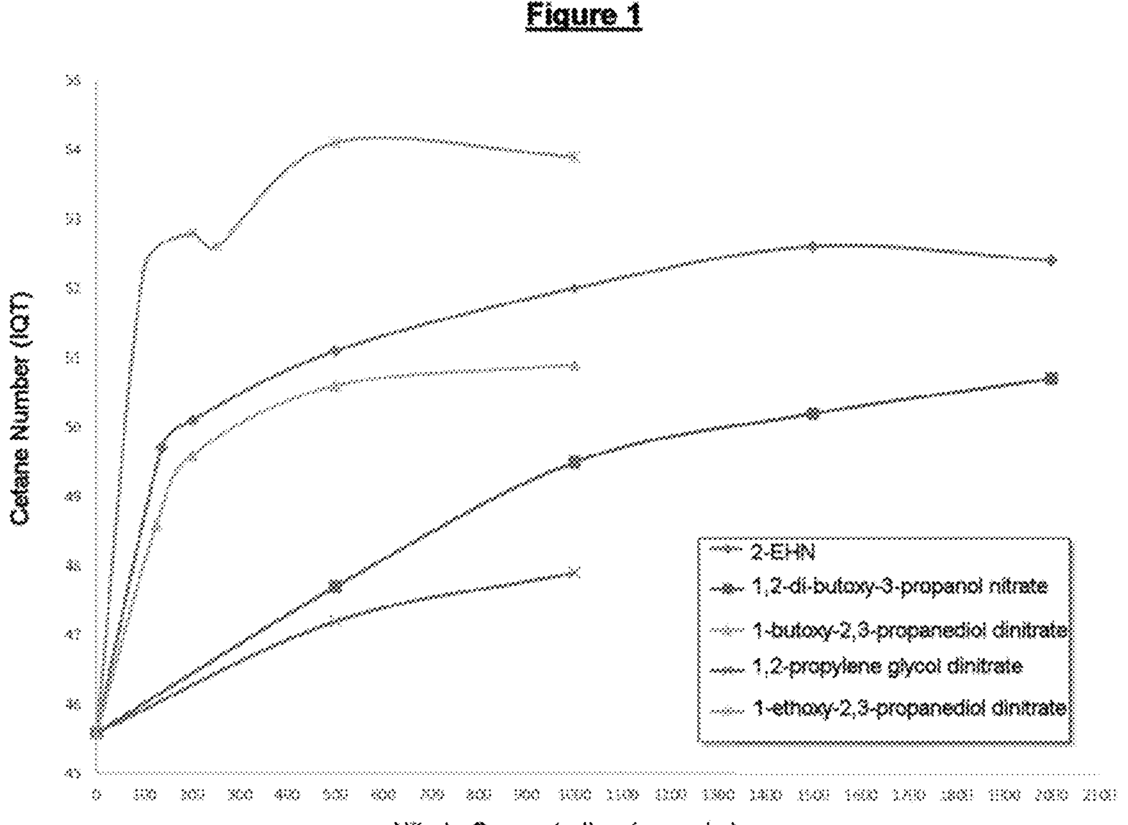
FIG. 1: a graph with results of tests carried out with the objective of evaluating the performance of different nitrates of glycerol ethers against 2-EHN (2-ethyl hexyl nitrate) in increasing the cetane number in S10 diesel (with up to 10 ppm sulfur).

The detailed description of the production process of the diesel cetane improver additive, from glycerol and ethanol, will be carried out according to the identification of the reagents and the steps of the obtaining process.

For a better understanding of the object of the present invention, diesel is considered to be a mixture of hydrocarbons, with a distillation range between 160° C. and 370° C. Glycerin is known by the traditional IUPAC nomenclature as propanetriol.

The present invention uses glycerin as a raw material for the synthesis of ethers that subsequently undergo a nitration process, according to the following steps:

(a) etherification reaction of glycerin with ethanol, at a temperature between 50° C. and 250° C., in liquid phase. In this step, acidic catalysts can be used, chosen from: ion exchange resins, zeolites, aluminas, niobic acid or others. The reaction takes place in batch reactors (STR), continuously fed (CSTR) or in a fixed bed. Preferably, the glycerol/ethanol molar ratio ranges from 1:1 to 1:6 and the space velocity (LHSV) ranges from 0.25 to 4.00 $h^{-1}$, depending on the catalytic system used. In this process, there are produced mono-ethers (1-ethoxy-2,3-propanediol, 2-ethoxy-1,3-propanediol), di-ethers (1,3-di-ethoxy-2-propanol, 1,2-di-ethoxy-3-propanol), tri-ethers (1,2,3-tri-ethoxy-propane), di-ethyl ether and water, with yields depending on the operating conditions used;

(b) after the etherification reaction, the reactor effluent is separated by traditional unit operations, such as flash, decantation and distillation, in order to obtain the glycerol and ethanol mono-ethers in a concentrated form. The glycerol di- and tri-ethers produced can be sent to the diesel pool or to other applications such as solvents and bases for paints and cleaning products. The di-ethyl ether formed could also be used as a fuel or in more specific applications;

(c) nitration of the glycerol and ethanol mono-ethers obtained in step (b). Nitration takes place at a temperature of −10 to 10° C., using a sulfonitric mixture (sulfuric oleum or concentrated sulfuric acid and concentrated nitric acid), with or without the addition of a cosolvent (dichloromethane, preferably, but not limited to this), a mixture of nitric acid and acetic anhydride, in a ratio of 30:70 to 50:50, with an excess of up to 200%. Alternatively, the nitration process can occur by means of the direct reaction with dinitrogen pentoxide ($N_2O_5$) or nitronium chloride;

(d) dilution of the mixture from step (c) with ice water, followed by a neutralization reaction, in which the organic phase is subjected to neutralization to pH 6.0, with an alkaline solution, at a temperature close to 0° C. In this step, the co-solvents and residual acids are recovered, while the dinitrated ethers are stabilized and are then ready for use.

In a first aspect, it should be highlighted that the compounds generated in step (a) are mono-ethers (1-ethoxy-2,3-propanediol; 2-ethoxy-1,3-propanediol), di-ethers (1,2-di-butoxy-3-propanol and 1,3-di-butoxy-2-propanol), and tri-ethers (tri-ethoxy-propane), as well as di-ethyl ether and water.

In a second aspect, it is highlighted that from step (b), a separation, a mixture of glycerol and ethanol mono-ethers is obtained, namely 1-ethoxy-2,3-propanediol and 2-ethoxy-1,3-propanediol, as well as a mixture of glycerol di- and tri-ethers and a di-ethyl ether stream.

In a third aspect, it is mentioned that the compounds resulting from step (d) are: 1-ethoxy-2,3-propadiol dinitrate and 2-ethoxy-1,3-propanediol dinitrate.

In a fourth aspect, it should be emphasized that the dinitrated ethers obtained in step (d) present unexpectedly superior results, as diesel cetane improvers, when compared to those obtained with 2-ethyl hexyl nitrate (2-EHN).

In a last aspect, the nitration process of glycerol and ethanol mono-ethers is processed in the reactor until the temperature stabilizes, indicating the end of the formation of a mixture of dinitrated ethers, in particular, 1-ethoxy-2,3-propanediol dinitrate or 2-ethoxy-1,3-propanediol dinitrate.

Figure 2:
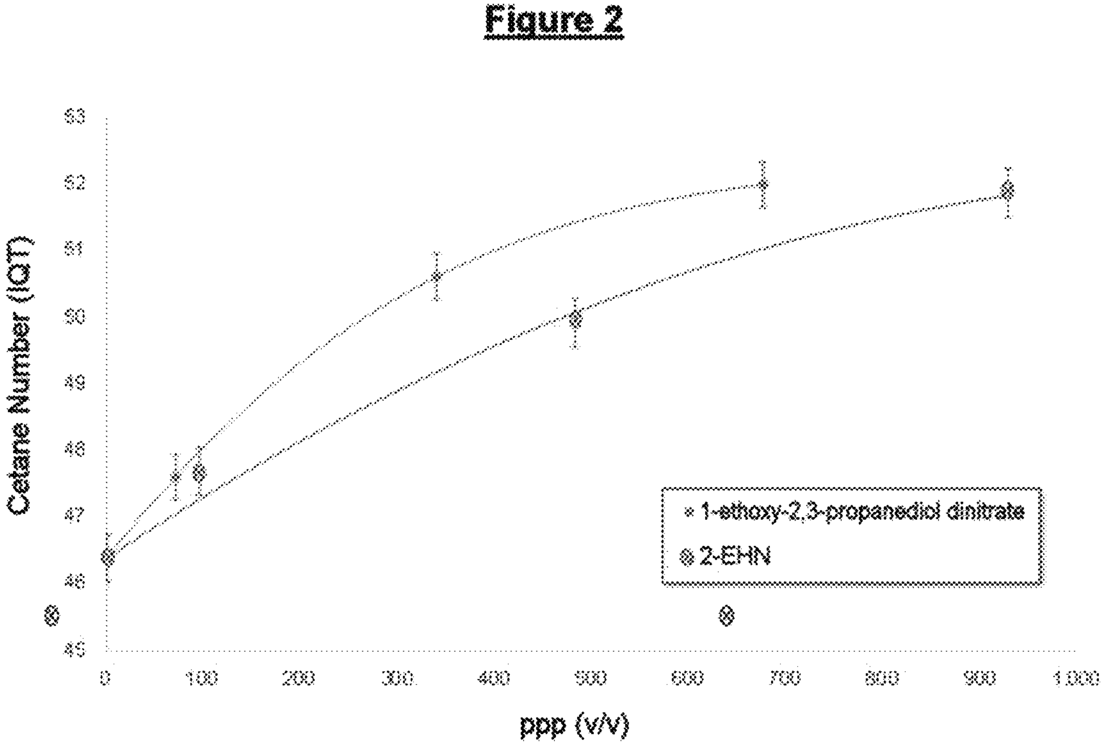
FIG. 2: graph with the results of tests carried out with the objective of evaluating the influence of the concentration of the additives 1-ethoxy-2,3-propanediol dinitrate and EHN (2-ethyl hexyl nitrate) on the increase in the cetane number of the S10 diesel (with up to 10 ppm sulfur).

As can be seen in FIGS. 1 and 2, the dinitrated glycerol and ethanol mono-ethers obtained in step (d) are compared with other nitrated additives used as diesel cetane number improvers. In these tests, it was observed that 1-ethoxy-2,3-propanediol dinitrate performed significantly better than 2-ethyl hexyl (2-EHN), the main commercial additive used.

Example 01

A sample of S10 diesel (with up to 10 ppm sulfur), with a cetane number of 45.8, was used to evaluate the performance of various cetane-improving additives. The additives studied were: 2-ethyl hexyl nitrate (2-EHN), considered to be the standard for diesel additives; 1,2-di-butoxy-3-propanol nitrate; 1-butoxy-2,3-propanediol dinitrate; 1,2-propylene glycol dinitrate and 1-ethoxy-2,3-propanediol dinitrate. For each type of additive, several samples were prepared with concentrations of additive varying from 100 to 2100 ppm by weight. The cetane number of each sample was evaluated by the ASTM D6890 method (Ignition Quality Test—IQT) and the results are shown in FIG. 1. It is observed that both glycerol tert-butyl ethers nitrated in one or two positions and 1,2-propylene glycol dinitrate showed lower performances than 2-ethyl hexyl nitrate (2-EHN).

It is verified that the mono-ether of glycerol and ethanol nitrated in two positions (1-ethoxy-2,3-propanediol dinitrate) performed much better than 2-EHN (2-ethyl hexyl nitrate) for all concentrations tested.

With regard to 1,2-propylene glycol dinitrate, it is noted that it has lower performance than 1,2-di-butoxy-3-propanol nitrate, despite having two nitro groups. This fact suggests that the greater polarity of this dinitrate should negatively influence its miscibility in diesel and, consequently, its performance as an additive.

In relation to 1-butoxy-2,3-propanediol dinitrate, it presented results well superior to 1,2-propylene glycol dinitrate, approximating to 2-EHN (2-ethyl hexyl nitrate). Possibly, this result can be explained by the lower polarity of 1-butoxy-2,3-propanediol compared to 1,2-propylene glycol dinitrate, allowing greater miscibility in diesel.

This said, one would not expect a better result from 1-ethoxy-2,3-propanediol dinitrate than that obtained from 1-butoxy-2,3-propanediol dinitrate, as they both have two nitro groups and the first is more polar than the second. However, what is observed is a much superior result for 1-ethoxy-2,3-propanediol dinitrate, which is even higher than 2-EHN (2-ethyl hexyl nitrate).

Example 02

In a second test, a sample of S10 diesel (up to 10 ppm of sulfur), of naphthenic base, with initial cetane number of 46.4, was used to compare the performance of 2-EHN (2-ethyl hexyl nitrate) and 1-ethoxy-2,3-propanediol dinitrate in different concentrations. The cetane number of each sample was evaluated by the ASTM D6890 method (Ignition Quality Test—IQT) and the results are shown in FIG. 2.

From these analyses, it was possible to confirm a better performance of glycerol and ethanol mono-ether dinitrate when compared to 2-EHN (2-ethyl hexyl nitrate).

Thus, to obtain cetane number 48, specification of S10 cetane by the ANP (Brazilian National Agency of Petroleum, Gas and Biofuels), approximately 200 ppm of 2-EHN (2-ethyl hexyl nitrate) would be needed, whereas to achieve the same cetane number, under the same conditions, only 100 ppm of 1-ethoxy-2,3-propanediol dinitrate would be needed.

It should be noted that, although the present invention has been described in relation to the attached figures, it may undergo modifications and adaptations by technicians skilled on the subject, depending on the specific situation, but provided that it is within the inventive scope defined herein.

The invention claimed is:

1. A PROCESS FOR OBTAINING NITRATES OF ETHERS OF GLYCEROL AND ETHANOL AS DIESEL CETANE IMPROVERS, comprising the following steps:

a) etherification reaction between glycerol and alcohols, wherein the alcohols comprises ethanol, and wherein the etherification reaction is catalyzed by an acidic catalyst chosen from: ion exchange resins, zeolites, aluminas, niobic acid or another acidic catalyst, and wherein the etherification reaction occurs with a glycerol/ethanol molar ratio ranging between 1:1 and 1:6, temperature between 5° and 250° C. and a space velocity (LHSV) from 0.25 to 4.00 $h^{-1}$;

b) separating the compounds obtained in step (a); and c) nitration of glycerol and ethanol mono-ethers, with the substitution of the two available hydroxyls, forming dinitrated ethers, using glycerin from a biodiesel production process.

2. THE PROCESS FOR OBTAINING NITRATES OF ETHERS OF GLYCEROL AND ETHANOL according to claim 1, wherein the etherification reaction is carried out in a batch reactor (STR), continuously fed (CSTR), fixed bed or reactive distillation.

3. THE PROCESS FOR OBTAINING NITRATES OF ETHERS OF GLYCEROL AND ETHANOL according to claim 1, wherein mono-ethers, (1-ethoxy-2,3-propanediol) are generated in step (a), 2-ethoxy-1,3-propanediol), di-ethers, (1,2-di-butoxy-3-propanol and 1,3-di-butoxy-2-propanol) and tri-ethers (tri-ethoxy-propane), as well as di-ethyl-ether and water.

4. THE PROCESS FOR OBTAINING NITRATES OF ETHERS OF GLYCEROL AND ETHANOL according to claim 1, wherein during step (b), the following streams are separated: mixture of glycerol and ethanol mono-ethers, namely 1-ethoxy-2,3-propanediol and 2-ethoxy-1,3-propanediol; a mixture of glycerol di- and tri-ethers (1,3-di-ethoxy-2-propanol, 1,2-di-ethoxy-3-propanol and 1,2,3-tri-ethoxy-propane) and di-ethyl ether.

5. THE PROCESS FOR OBTAINING NITRATES OF ETHERS OF GLYCEROL AND ETHANOL according to claim 1, wherein the nitration step of glycerol and ethanol mono-ethers occurs at temperatures in the range between −10° C. and 10° C.

6. THE PROCESS FOR OBTAINING NITRATES OF ETHERS OF GLYCEROL AND ETHANOL according to claim 1, wherein the nitration step of the glycerol and ethanol mono-ethers uses a sulfonitric mixture (sulfuric oleum or concentrated sulfuric acid and concentrated nitric acid).

7. THE PROCESS FOR OBTAINING NITRATES OF ETHERS OF GLYCEROL AND ETHANOL according to claim 1, wherein the nitration step of glycerol and ethanol mono-ethers occurs by direct reaction with dinitrogen pentoxide or nitronium chloride.

8. THE PROCESS FOR OBTAINING NITRATES OF ETHERS OF GLYCEROL AND ETHANOL according to claim 1, wherein in the nitration step of glycerol and ethanol mono-ethers, occurs the formation of a mixture of dinitrated ethers, specifically, 1-ethoxy-2,3-propanediol dinitrate or 2-ethoxy-1,3-propanediol dinitrate.

9. THE PROCESS FOR OBTAINING NITRATES OF ETHERS OF GLYCEROL AND ETHANOL according to claim 6, further comprising the addition of a cosolvent, mixture of nitric acid and acetic anhydride, in a ratio of 30:70 to 50:50, with an excess of up to 200%.

10. THE PROCESS FOR OBTAINING NITRATES OF ETHERS OF GLYCEROL AND ETHANOL according to claim 9, wherein the cosolvent is dichloromethane.

* * * * *